(12) United States Patent
Pan et al.

(10) Patent No.: US 11,324,678 B2
(45) Date of Patent: *May 10, 2022

(54) CORE SHELL SILICA PARTICLES AND USES THEREOF AS AN ANTI-BACTERIAL AGENT

(71) Applicant: Colgate-Palmolive Company, New York, NY (US)

(72) Inventors: Guisheng Pan, Philadelphia, PA (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/512,472

(22) Filed: Jul. 16, 2019

(65) Prior Publication Data

US 2019/0336419 A1 Nov. 7, 2019

Related U.S. Application Data

(63) Continuation of application No. 15/106,445, filed as application No. PCT/US2014/071298 on Dec. 18, 2014, now Pat. No. 10,369,091.

(Continued)

(51) Int. Cl.
*A61K 8/25* (2006.01)
*A61Q 11/00* (2006.01)
(Continued)

(52) U.S. Cl.
CPC ............. *A61K 8/25* (2013.01); *A61K 8/022* (2013.01); *A61K 8/0241* (2013.01);
(Continued)

(58) Field of Classification Search
CPC ................................. A61K 8/25; A61Q 11/00
See application file for complete search history.

(56) References Cited

U.S. PATENT DOCUMENTS 2,885,366 A 5/1959 Iler
2,913,419 A 11/1959 Alexander
(Continued)

FOREIGN PATENT DOCUMENTS

CN 86102002 9/1986
CN 1221393 6/1999
(Continued)

OTHER PUBLICATIONS

SA Greenberg. "The Depolymerization of Silica in Sodium Hydroxide Solutions." Journal of Physical Chemistry, vol. 61(7), pp. 960-965. (Year: 1957).*

(Continued)

*Primary Examiner* — Isaac Shomer

(57) ABSTRACT

This invention provides core shell silica particles, wherein each core shell silica particle comprises a silica core, and a surface of the silica core etched with group I metal silicate. These core shell silica particles have high surface charge density and anti-bacterial activity. Also provided are compositions comprising core shell silica particles, process of making the core shell silica particles and methods of reducing or inhibiting bacterial activity by administering the core shell silica particles or compositions thereof.

18 Claims, 3 Drawing Sheets

Related U.S. Application Data

(60) Provisional application No. 61/918,938, filed on Dec. 20, 2013, provisional application No. 61/918,925, filed on Dec. 20, 2013.

(51) Int. Cl.

| | |
|---|---|
| *A61K 8/02* | (2006.01) |
| *A61K 8/19* | (2006.01) |
| *C01B 33/18* | (2006.01) |
| *C03C 15/00* | (2006.01) |
| *C09C 1/30* | (2006.01) |
| *A61K 8/46* | (2006.01) |
| *C03C 17/23* | (2006.01) |
| *C09K 3/14* | (2006.01) |
| *C03C 17/22* | (2006.01) |

(52) U.S. Cl.
CPC .......... *A61K 8/0245* (2013.01); *A61K 8/0258* (2013.01); *A61K 8/19* (2013.01); *A61K 8/466* (2013.01); *A61Q 11/00* (2013.01); *C01B 33/18* (2013.01); *C03C 15/00* (2013.01); *C03C 17/22* (2013.01); *C03C 17/23* (2013.01); *C09C 1/3054* (2013.01); *C09K 3/1436* (2013.01); *C09K 3/1445* (2013.01); *A61K 2800/28* (2013.01); *A61K 2800/621* (2013.01); *A61K 2800/651* (2013.01); *A61K 2800/92* (2013.01); *C01P 2004/61* (2013.01); *C01P 2004/84* (2013.01)

(56) References Cited

U.S. PATENT DOCUMENTS

| | | | |
|---|---|---|---|
| 3,537,815 A | 11/1970 | Burke | |
| 3,655,578 A | 4/1972 | Yates | |
| 3,725,095 A | 4/1973 | Weidman et al. | |
| 3,922,393 A | 11/1975 | Sears, Jr. | |
| 3,924,030 A | 12/1975 | Iwasa et al. | |
| 4,038,380 A | 7/1977 | Cordon | |
| 4,336,245 A | 6/1982 | Wason | |
| 4,340,583 A | 7/1982 | Wason | |
| 4,568,540 A | 2/1986 | Asano et al. | |
| 5,413,844 A | 5/1995 | Persello | |
| 5,512,094 A | 4/1996 | Linton | |
| 5,537,363 A | 7/1996 | Holcomb | |
| 5,658,573 A * | 8/1997 | Holcomb | A21D 2/02 424/400 |
| 5,948,383 A | 9/1999 | Kuznicki et al. | |
| 6,030,222 A | 2/2000 | Tarver | |
| 6,221,326 B1 | 4/2001 | Amiche | |
| 6,632,853 B2 | 10/2003 | Alkemper et al. | |
| 6,660,380 B1 * | 12/2003 | Ishida | A61Q 17/04 428/403 |
| 7,125,432 B2 | 10/2006 | Huang | |
| 7,267,814 B2 | 9/2007 | McGill et al. | |
| 7,297,327 B2 | 11/2007 | Pilch et al. | |
| 7,402,416 B2 | 7/2008 | Szeles et al. | |
| 7,857,985 B2 | 12/2010 | Ishima et al. | |
| 8,118,898 B2 | 2/2012 | Wakamiya et al. | |
| 8,221,791 B1 * | 7/2012 | Santra | A61K 9/5115 424/484 |
| 8,609,068 B2 | 12/2013 | Hagar et al. | |
| 8,840,911 B2 | 9/2014 | Flugge-Berendes et al. | |
| 9,028,605 B2 | 5/2015 | Hagar et al. | |
| 10,064,794 B2 | 9/2018 | Xu et al. | |
| 10,369,091 B2 * | 8/2019 | Pan | A61K 8/0258 |
| 10,596,084 B2 * | 3/2020 | Maloney | A61K 8/345 |
| 2002/0168324 A1 | 11/2002 | Amiche et al. | |
| 2005/0112161 A1 * | 5/2005 | Luo | A61K 8/602 424/401 |
| 2006/0011337 A1 | 1/2006 | Paul | |
| 2006/0034780 A1 | 2/2006 | Guan et al. | |
| 2006/0110307 A1 | 5/2006 | McGill et al. | |
| 2006/0283095 A1 * | 12/2006 | Mahulikar | C01B 33/22 51/308 |
| 2007/0086960 A1 | 4/2007 | Tarver et al. | |
| 2007/0275257 A1 | 11/2007 | Muraguchi et al. | |
| 2008/0086951 A1 * | 4/2008 | Wakamiya | C09K 3/1436 51/308 |
| 2008/0152599 A1 | 6/2008 | Brignoli et al. | |
| 2009/0226498 A1 * | 9/2009 | Flugge-Berendes | A61K 31/045 424/411 |
| 2010/0189663 A1 | 7/2010 | Gallis et al. | |
| 2012/0021034 A1 * | 1/2012 | Zink | A01N 59/16 424/421 |
| 2012/0052025 A1 * | 3/2012 | Porter | A61P 29/00 424/52 |
| 2013/0129642 A1 | 5/2013 | Joiner et al. | |
| 2013/0280409 A1 | 10/2013 | Mushock et al. | |
| 2016/0296434 A1 | 10/2016 | Fei et al. | |

FOREIGN PATENT DOCUMENTS

| | | | |
|---|---|---|---|
| CN | 1625383 | 6/2005 | |
| CN | 1625383 A | 6/2005 | |
| CN | 1695447 | 11/2005 | |
| CN | 1739483 | 3/2006 | |
| CN | 1953658 | 4/2007 | |
| CN | 103274422 | 9/2013 | |
| CN | 103342368 | 10/2013 | |
| EP | 345116 | 12/1989 | |
| EP | 0345116 | 12/1989 | |
| EP | 1935395 | 6/2008 | |
| EP | 1837903 | 11/2009 | |
| GB | 804486 | 11/1958 | |
| JP | H11-511178 | 9/1999 | |
| JP | H11-511178 A | 9/1999 | |
| JP | 2002-047158 | 2/2002 | |
| JP | 2016519077 | 6/2016 | |
| KR | 20030061874 | 7/2003 | |
| KR | 20110103934 | 9/2011 | |
| KR | 20130074422 | 7/2013 | |
| RU | 2275183 | 4/2006 | |
| RU | 2485941 | 6/2013 | |
| RU | 2496716 | 10/2013 | |
| RU | 2582945 | 4/2016 | |
| TW | 200745267 | 12/2007 | |
| WO | 1994/006868 | 3/1994 | |
| WO | 1997/046485 | 12/1997 | |
| WO | WO-0249588 A2 * | 6/2002 | ............ A61K 8/731 |
| WO | 2005/107456 | 11/2005 | |
| WO | 2009/001697 | 12/2008 | |
| WO | 2009/112458 | 9/2009 | |
| WO | 2012/031785 | 3/2012 | |
| WO | 2012/110995 | 8/2012 | |
| WO | 2013/089759 | 6/2013 | |
| WO | 2015/076817 | 5/2015 | |

OTHER PUBLICATIONS

M Fertani-Gmati, M Jemal. "Thermochemistry and kinetics of silica dissolution in NaOH aqueous solution." Thermochimica Acta, vol. 513, pp. 43-48. (Year: 2011).*

Y Niibori, M Kunita, O Tochiyama, T Chida. "Dissolution Rates of Amorphous Silica in Highly Alkaline Solution." Journal of Nuclear Science and Technology, vol. 37 No. 4, pp. 349-357. (Year: 2000).*

J.M. Rimsza, R.E. Jones, L.J. Criscenti. "Interaction of NaOH solutions with silica surfaces." Journal of Colloid and Interface Science vol. 516 (2018), pp. 128-137. (Year: 2018).*

CaseText. "*Holcomb Health Care Services, LLC v. Quart Limited, LLC* (In re Holcomb Health Care Services, LLC)." https://casetext.com/case/in-re-holcomb-health-care-services downloaded on Dec. 9, 2020, originally published Dec. 14, 2004, pp. 1-79. (Year: 2004).*

Alexei Smirnov. "Legal dispute over Holcomb intellectual property expands." The Nashville Post, https://www.nashvillepost.com/home/article/20448692/legal-dispute-over-holcomb-intellectual-property-expands downloaded Dec. 9, 2020, published Apr. 1, 2004, pp. 1-3. (Year: 2004).*

(56) References Cited

OTHER PUBLICATIONS

Alexei Smirnov. "Judge Paine hands down Holcomb Healthcare opinion." The Nashville Post, https://www.nashvillepost.com/business/health-care/medical-devices/article/20449550/judge-paine-hands-down-holcomb-healthcare-opinion downloaded Dec. 9, 2020, originally published Dec. 16, 2004, pp. 1-2. (Year: 2004).*

Lanlang Corporation, https://www.lanlangcorp.com/info/strong-base-anion-exchange-resin-example-41908792.html accessed Aug. 25, 2021, originally published Dec. 24, 2019, 5 printed pages. (Year: 2019).*

Anna Torrado, Manuel Valiente, Carlos A. Munoz. "Cleaning power and abrasivity of a new toothpaste based on ion-exchange resins." American Journal ofDentislly, vol. 17, No. 2, Apr. 2004, pp. 80-84. (Year: 2004).*

Angelo C. Pinto et al. "Separation of Acid Diterpenes of Copaifera cearensis Huber ex Ducke by Flash Chromatography Using Potassium Hydroxide Impregnated Silica Gel." Journal of the Brazilian Chemical Society, vol. 11, No. 4, 2000, pp. 355-360. (Year: 2000).*

Sten Ahrland, Ingmar Grenthe, and Bertil Noren. "The Ion Exchange Properties of Silica Gel, II. Separation of Plutonium and Fission Products from Irradiated Uranium." Acta Chemica Scandinavica, vol. 14, 1960, pp. 1077-1090. (Year: 1960).*

Supelco. http://www.supelco.com.tw/B-11-Resins.pdf accessed Dec. 13, 2021, pp. 429-456. (Year: 2021).*

BYU Cleanroom. KOH Etching. https://cleanroom.byu.edu/KOH accessed Sep. 27, 2018, 20 printed pages. (Year: 2018).

Cardinal Search Report, dated 2013, "Chemically Modified SiO2 Practical in Dental Products".

Cardinal Search Report, dated 2013, "Chemically modified SiO2 practical in dental products," Supplemental Search.

Choksi et al., 2013, "A research review article on composite material," Asian Academy Researach J. Multidiscip. 1 (8):44-56.

Ciriminna et al., 2013, "The sol-gel route to advanced silica-based materials and recent applications" Chemical Reviews 113:6592-6620.

English translation of CN 1695447 A. Patent originally published in Chinese on Nov. 16, 2005. Translation Jun. 13, 2017. 6 printed pages.

Gahlaut et al., 2013, "Evaluation of antibacterial potential of plant extracts using Resazurin based microtiter dilution assay," International Journal of Pharmacy and Pharmaceutical Sciences 5(2):372-376.

International Search Report and Written Opinion of the International Searching Authority in International Application No. PCT/US2014/071298, dated May 28, 2015.

International Search Report and Written Opinion of the International Searching Authority in International Application No. PCT/US2014/071304, dated May 28, 2015.

International Search Report and Written Opinion of the International Searching Authority in International Application No. PCT/US2014/071502, dated Apr. 22, 2015.

International Search Report and Written Opinion of the International Searching Authority in International Application No. PCT/US2014/071511, dated Apr. 22, 2015.

J Yamanaka, Y Hayashi, N Ise, T Yamaguchi. "Control of the surface charge density of colloidal silica by sodium hydroxide in salt-free and low-salt dispersions." Physical Review E, vol. 55 No. 3, Mar. 1997, pp. 3028-3036. (Year: 1997).

Zhang et al., 2009, "Rattle-type silica colloidal particles prepared by a surface-protected etching process," Nano Research 2:583-591.

Zhuravlev, 2000, "The surface chemistry of amorphous silica. Zhuravlev model," Colloids and Surfaces: A: Physiochem. Eng. Aspects, 173:1-38.

International Search Report and Written Opinion of the International Searching Authority in International Application No. PCT/US2017/067296, dated Mar. 23, 2018.

* cited by examiner

CORE SHELL SILICA PARTICLES AND USES THEREOF AS AN ANTI-BACTERIAL AGENT

BACKGROUND

Silica (SiO$_2$) particles are commonly used as abrasive and/or thickeners in oral care compositions usually in the form of fumed silica or precipitated silica. One of the benefits of using silica is their low cost. However, silica has limited utility besides its abrasive and/or thickening effect. As a result, other active agents must be added to an oral care composition to provide a desired effect (e.g., adding an anti-bacterial agent to provide an anti-bacterial effect, adding tartar-control agents for tartar control). The need to add other active agents not only raises the possibility that the oral care composition will not meet regulatory burdens which can arise when the other active agents are used, but also increases the possibility that the oral care composition will not be desirable to the user of the composition (e.g. user sensitivity to the surfactant sodium lauryl sulfate (SLS), user aversion to the taste of a zinc compound, salty flavor and crystallization issues with current tartar-control agents etc.). Moreover, further problems may arise. For example, a common problem with the use of an anti-bacterial agent is the development of resistance by bacteria to the agent.

Core-shell structured colloidal particles have been known for several decades. The most famous example is the light-diffracting precious Opal which is formed slowly in several thousand years in natural environments. Its core-shell structures were discovered by electron microscope in 1960s. Various synthetic core-shell colloidal particles have been made since then. However, the synthesis of such core-shell materials is often complex, requiring multistep coating methodologies (See Kalele et al, "Nanoshell particles: synthesis, properties and applications", current science, vol. 91, no. 8, 25 Oct. 2006). Therefore although the core-shell technology has been known for several decades, it has not yet been applied in the dentifrice industry, probably due to the high cost of making the CSS abrasive materials.

Therefore, there is still a need in the art for oral care compositions with multifunctional effects, but with a minimum of ingredients necessary to achieve the multifunctional effects. There is also still a need to develop additional anti-bacterial agents and tartar control agents suitable for use in oral care compositions.

BRIEF SUMMARY

The present invention relates to core shell silica particles, wherein each core shell silica particle comprises a silica core, and a surface of the silica core etched with group I metal silicate.

The present invention also relates to compositions comprising the core shell silica particles.

The present invention also relates to the process for making the core shell particles which comprises admixing an amount of silica particles in water with an amount of base, wherein the base comprises a group I metal ion, to produce the core shell silica particles.

The present invention also relates to a method for reducing or inhibiting bacteria in the oral cavity of a patient in need thereof, which comprises applying to the oral surfaces of the patient the composition of the invention.

Reference to metal CSS particles refer to the metal with the appropriate +1 charge, e.g. for Na-CSS, the Na is Na+, for K-CSS, the K is K+, etc.

As used throughout, ranges are used as shorthand for describing each and every value that is within the range, and for describing sub-ranges within the range. Any value within the range can be selected as the upper terminus of the sub-range. Any value within the range can be selected as the lower terminus of the sub-range.

In addition, all references, books, patents, and patent application publications cited herein are hereby incorporated by reference in their entireties. In the event of a conflict in a definition in the present disclosure and that of a cited reference, book, patent, or patent application publication, the present disclosure controls.

Unless otherwise specified, reference to ambient or room temperature refers to a temperature range of 20-25° C.

Unless otherwise specified, all percentages and amounts expressed herein and elsewhere in the specification should be understood to refer to percentages by weight based on the total weight of the composition.

The phrase "and/or" as used herein, with option A and/or option B for example, encompasses the individual embodiments of (i) option A; (ii) option B; and (iii) option A plus option B.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group and all possible subgroups of the main group, but also the main group absent one or more of the group members. The present invention also envisages the explicit exclusion of one or more of any of the group members in the claimed invention.

All combinations of the various elements described herein are within the scope of the invention unless otherwise indicated herein or otherwise clearly contradicted by context.

Further areas of applicability of the present invention will become apparent from the detailed description provided hereinafter. It should be understood that the detailed description and specific examples are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

Description of the Core Shell Silica Particles

The present invention provides core shell silica particles, wherein each core shell silica particle comprises a silica core, and a surface of the silica core etched with group I metal silicate.

Core shell silica particles are prepared by etching silica ($SiO_2$) with a base to form core(Silica)-shell(metal silicate) structured colloids. For example using NaOH as the base, core($SiO_2$)-shell($Na_2SiO_3$) structured colloids are formed. The reaction is as follows:

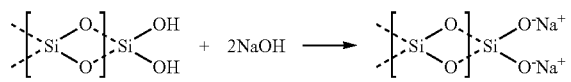

The $Na_2SiO_3$ molecules (contributing 2 negative charges with 2 Na+ counter ions) on colloidal core-shell silica particle surface.

A surface of the silica core is etched with metal silicate. The term "etched" means that a surface of the silica core is dissolved, and group I metal silicate is formed on top of the silica core. The process for making the core shell silica (CSS) particles of the invention comprises etching the original silica in order to form the $Na_2SiO_3$. The reaction of the silica particle with base causes a reduction in the diameter of the silica particle to form a silica core, and group I metal silicate is formed on top of the silica core. The $Na_2SiO_3$ layers are not additional layers coated on top of the original surface of the silica.

Methods of forming particles by coating silica with silicate are described in the prior art (e.g. Kalele et al, "Nanoshell particles: synthesis, properties and applications", current science, vol. 91, no. 8, 25 Oct. 2006). However, these methods of preparing silica/silicate particles are more complex, costly and different than etching the methods described in the present application.

The metal silicate typically comprises the formula $M_2SiO_3 \cdot xH_2O$, wherein M is a group I metal, and x is from 0 to 10. The metal silicate may be anhydrous, i.e. x=0, or may be hydrated. Preferably, M is Na or K.

Figure 1:
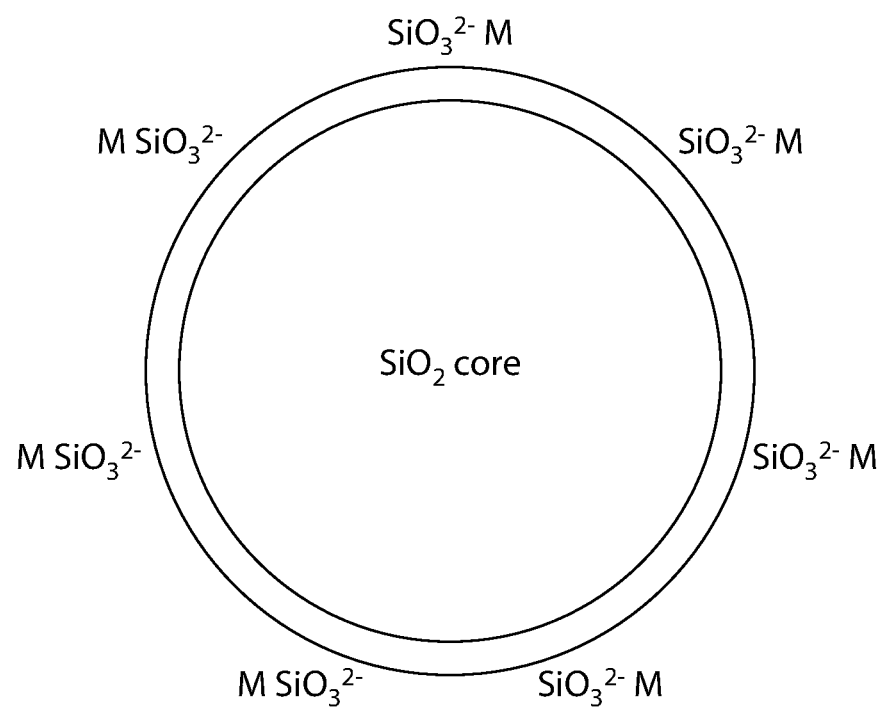
FIG. 1 shows a schematic of a core shell silica particle of the invention.

The surface of the silica core may be the outer surface of the silica core (see FIG. 1A).

Figure 2:
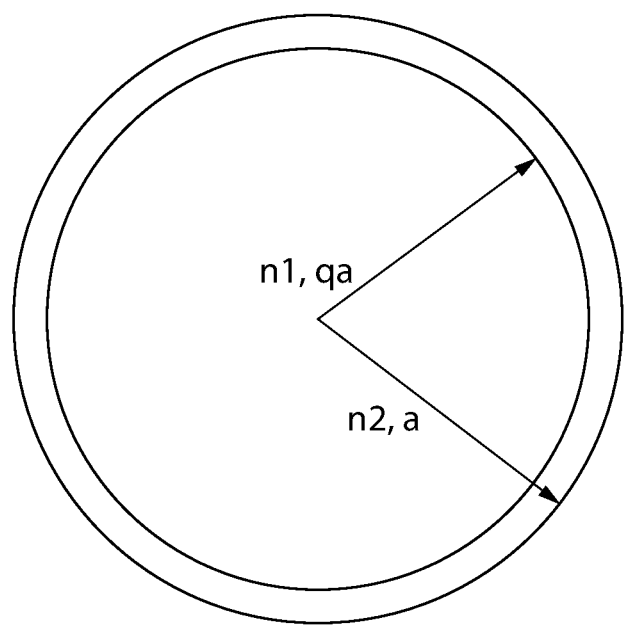
FIG. 2 shows a schematic of a core shell silica particle showing parameters defined in the light scattering model according to an aspect of the invention.

Alternatively, or in addition, the surface of the silica core may be an internal surface of the silica core (see FIG. 2).

In one embodiment the outer 10 nm depth of each particle comprises from 0.1 to 10, optionally 0.1 to 2 weight % $M_2SiO_3 \cdot xH_2O$.

In one embodiment the outer 10 nm depth of each particle has the general formula:

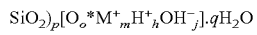

wherein O* is oxygen in the silicate form; M is a group I metal ion; p, o, m, h, j and q are the atomic percentages of each component (p is the atomic percentage of $SiO_2$, O is the atomic percentage of oxygen in the silicate form, m is the atomic percentage of group I metal, h is the atomic percentage of $H^+$, j is the atomic percentage of OFF, and q is the atomic percentage of $H_2O$); and the total charge of each core shell silica particle is zero.

Typically the atomic percentage for each component except H+ is determined by electron spectroscopy for chemical analysis (ESCA).

Optionally, the outer 10 nm depth of each particle has one of the following compositions:

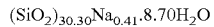

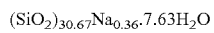

The d(0.5) or d50 of the particles is the diameter (typically in microns) that splits the distribution with half the population above and half below this diameter. It will be noted that this parameter is a value for a population of particles, and that the diameter of an individual particle may be larger or smaller than the d(0.5) values described herein. The Dv50 (or Dv0.5) is the median for a volume distribution, Dn50 is used for number distributions, and Ds50 is used for surface distributions. In the present context, d(0.5) will be used to refer to the median particle size for a volume distribution.

In one embodiment, the d(0.5) value of the CSS particles is from 5 nm to 50 μm.

In another embodiment, the d(0.5) value of the CSS particles may be from 26 μm to 40 μm. Particles having a d(0.5) value within this range are typically translucent. Translucent particles are those which allow light to pass through, although it is not possible to see an image through the particles. This is distinguished from transparent compositions which allow light to pass through and an image can be seen through the composition. Methods for determine particle size are well known in the art. For example particle size may be determined using light scattering methodologies, such as using the Mastersizer 2000, Hydro 2000S, Malvern Instruments Limited.

In another embodiment, the d(0.5) value of the CSS particles may be from 18 μm to 25 μm. Particles having a d(0.5) value within this range are typically semi-opaque.

In another embodiment, the d(0.5) value of the CSS particles may be from 10 μm to 15 μm. Particles having a d(0.5) value within this range are typically opaque.

In another embodiment, the d(0.5) value of the CSS particles may be from 5 μm to 15 μm.

In another embodiment, the d(0.5) value of the CSS particles may be from 2.5 μm to 4.5 μm.

In another embodiment, the d(0.5) value of the CSS particles may be from 5 nm to 20 nm.

In another embodiment, the d(0.5) value of the CSS particles may be from 10 nm to 15 nm.

The d(0.1) value of the CSS particles is the diameter that splits the distribution with 10% of the population below and 90% above this diameter.

The d(0.9) value of the CSS particles is the diameter that splits the distribution with 90% of the population below and 10% above this diameter.

A value used to describe the distribution width of the particle size distribution is the span:

$$\text{Span} = (d(0.9) - d(0.1))/d(0.5)$$

The span of the core shell silica particles according to the present invention is typically from 1.5 to 3.

In a preferred embodiment, the CSS have a d(0.1) of from 10 to 13 μm, a d(0.5) of from 30 to 33 μm, and a d(0.9) of from 61 to 64 μm.

In another preferred embodiment, the CSS have a d(0.1) of from 6 to 9 μm, a d(0.5) of from 18 to 21 μm, and a d(0.9) of from 41 to 45 μm.

In a further preferred embodiment, the CSS have a d(0.1) of from 3 to 5 μm, a d(0.5) of from 11 to 14 μm, and a d(0.9) of from 33 to 36 μm.

In preferred embodiments, the d(0.5) value of the CSS particles is less than the mean diameter of a human dentin tubule. This allows the CSS particles to enter the dentin tubules, which may be exposed on damage to the protective enamel layer. In human teeth, dentin tubule mean diameter near the dentino-enamel junction is 0.9 μm, the middle section of the dentin tubule has a diameter of about 1.2 μm and near the pulp the diameter is about 2.5 μm.

In another embodiment of the invention, a silica source is selected to produce CSS particles which fits into the dentin tubule (e.g. Aerosil® 200—a fumed silica (synthetic amorphous silica) with a d(0.5) of 0.012 µm). In another embodiment of the invention, the d(0.5) value of the CSS particles is less than 0.9 µm. In still another embodiment of the invention, the CSS particle has a d(0.5) in the range of 0.010 µm—less than 0.9 µm. In another embodiment of the invention, the CSS particles of the invention can also plug, block holes in the enamel.

CSS particles may be spherical, or substantially spherical however it will be understood that the particles may have other shapes, for example rod, needle, or ellipsoidal shapes. The particles may have irregular shapes. The particles may also form larger size aggregates.

The $M_2SiO_3.xH_2O$ may comprise a plurality of monolayers of $M_2SiO_3.xH_2O$. The number of monolayers may be from 2 to 100, from 2 to 40, 2 to 12 or 12 to 40 monolayers.

The particle may comprise 2, 4, 16, 32 or 36 surface $M_2SiO_3.xH_2O$ monolayers.

The silica is preferably selected from the group consisting of a precipitated silica, a fumed silica and a fused silica.

Core shell silica particles preferably have a high surface charge density and ion exchange capacity. Optionally, the core shell silica particles have a total cationic exchange capacity of from 0.5 to 5.0 meq/g.

In one embodiment, the core shell silica particles have a turbidity of from 0.0 to 0.2 at a wavelength of from 300 to 800 nm using a 0.20 mm quartz UV optical cell. These particles may be described as translucent or transparent.

In another embodiment, the core shell silica particles have a turbidity of from 0.8 to 1.6 at a wavelength of from 300 to 800 nm using a 0.20 mm quartz UV optical cell. These particles may be described as semi-opaque.

In a further embodiment, the core shell silica particles have a turbidity of from 1.8 to 2.4 at a wavelength of from 300 to 800 nm using a 0.20 mm quartz UV optical cell. These particles may be described as opaque.

In a further aspect, the present invention provides a composition comprising the core shell silica particles described above.

The composition may be a powder abrasive. This composition does not comprise a humectant.

The composition may comprise the core shell silica particles defined above and a carrier.

Preferably, the composition is an oral care composition and further comprises an orally acceptable carrier.

The oral care composition is in form of a solid, paste, gel composition or liquid composition. The composition may take any dosage form useful for oral administration. Illustrative examples of these include, but are not limited to, a dentifrice, e.g., a toothpaste, dental gel, dental cream, or tooth powder; a mouthwash, mouth rinse, or mouth spray; an oral slurry or liquid dentifrice; a gum or other confectionary; a lozenge; dental floss or dental tape; a prophylaxis paste or powder; a mono- or multi-layer oral film or gel strip, e.g., tooth strips or breath strips, preferably using a biodegradable or orally consumable film or gel; functional film or gel flakes or functional micro-, or nano-particles; a film-forming composition comprising pre-gel(s) or pre-polymer(s), e.g., film-forming dentifrices, dental paints; a tooth hardener; or a coating on an oral, e.g., orthodontic, appliance or implant.

The orally acceptable carrier is preferably water.

For solid dentifrices such as toothpastes, the amount of water in the composition is selected from an amount consisting of less than 10% by weight, less than 5% by weight, less than 1% by weight. In each of these amounts, the lower range for the amount of water is 0% or no more than 0.1% water.

The orally acceptable carrier may further comprise a humectant. The humectant may be ethanol, a polyhydric alcohol, which includes, but is not limited to glycerin, glycol, inositol, maltitol, mannitol, sorbitol, xylitol, propylene glycol, polypropylene glycol (PPG), polyethylene glycol (PEG) and mixtures thereof, and a saccharide, which includes, but is not limited to fructose, glucose, sucrose and mixtures of saccharides (e.g. honey).

In an embodiment of the composition, the core shell silica particles are present in an amount of from 0.1 wt % to 35 wt %, based on the weight of the composition. In another embodiment of the composition, the CSS particles are present in an amount from 0.1% to 1%. In another embodiment of the composition, the CSS particles are present in an amount from 0.5% wt. % to 20 wt. %, In another embodiment of the composition, the CSS particles are present in an amount from 1% wt. % to 10 wt. %.

In an embodiment of the composition comprising a carrier, the refractive index of the core shell silica particles is within ±0.1 units of the refractive index of the carrier.

The carrier may include, but is not limited to water or other aqueous solvent systems.

The oral care composition may further comprise an antibacterial agent. Possible anti-bacterial agents include, but are not limited to triclosan (5-chloro-2-(2,4-dichlorophenoxy)phenol); 8-hydroxyquinoline and salts thereof, zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof.

A further illustrative list of useful antibacterial agents is provided in U.S. Pat. No. 5,776,435, which is incorporated herein by reference. A further illustrative list of zinc ion sources include, but is not limited to the zinc salts include, but are not limited to zinc acetate, zinc borate, zinc butyrate, zinc carbonate, zinc chloride, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate and mixtures thereof.

In some embodiments, the anti-bacterial agent is present at a concentration selected from the group consisting of from 0.001% to 3%, by weight, 0.05% to 2%, by weight and 0.075% to 1.5% by weight.

In one embodiment there is no additional anti-bacterial agent except for the core shell silica particles of the invention.

The composition may further include anti-caries agents, desensitizing agents, viscosity modifiers, diluents, surfactants, emulsifiers, foam modulators, pH modifying agents, abrasives, mouth feel agents, sweetening agents, flavor agents, colorants, preservatives, amino acids, anti-oxidants, anti-calculus agents, a source of fluoride ions, thickeners, an active agent for prevention or treatment of a condition or disorder of hard or soft tissue of the oral cavity, and adhesive agent, a whitening agent and combinations thereof.

It is understood that while general attributes of each of the above categories of materials may differ, there may be some common attributes and any given material may serve multiple purposes within two or more of such categories of materials. Preferably, the carrier is selected for compatibility with other ingredients of the composition.

An embodiment of the composition optionally comprises an amino acid. Suitable amino acids include, but are not limited to arginine, cysteine, leucine, isoleucine, lysine, alanine, asparagine, aspartate, phenylalanine, glutamate, glutamic acid, threonine, glutamine, tryptophan, glycine, valine, praline, serine, tyrosine, and histidine, and a combination of two or more thereof. The amino acids can include R- and L-forms and salt forms thereof. The amino acids (and salt forms thereof) can also include ester and/or fatty amide derivatives of the amino acid (e.g. ethyl lauroyl arginate hydrochloride (ELAH)).

An embodiment of the composition optionally comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

An embodiment of the composition optionally comprises an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The anticalculus agent is present at about 0.1% to about 30%. The oral composition may include a mixture of different anticalculus agents. In one preferred embodiment, tetrasodium pyrophosphate (TSPP) and sodium tripolyphosphate (STPP) are used. The anticalculus agent comprises TSPP at about 1-2% and STPP at about 7% to about 10%.

An embodiment of the composition optionally comprises at least one orally acceptable source of fluoride ions. Any known or to be developed in the art may be used. Suitable sources of fluoride ions include fluoride, stannous fluoride, sodium fluoride, potassium fluoride, amine fluoride, ammonium fluoride, stannous monofluorophosphate, sodium monofluorophosphate, potassium monofluorophosphate, amine monofluorophosphate, ammonium monofluorophosphate, stannous fluorosilicate, sodium fluorosilicate, potassium fluorosilicate, amine fluorosilicate ammonium fluorosilicate, and mixtures thereof. One or more fluoride ion-releasing compound is optionally present in an amount providing a total of about 100 to about 20,000 ppm, about 200 to about 5,000 ppm, or about 500 to about 2,500 ppm, fluoride ions.

An embodiment of the composition optionally comprises various dentifrice ingredients to adjust the rheology and feel of the composition such as surface active agents, thickening or gelling agents, etc.

An embodiment of the composition optionally comprises a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

An embodiment of the composition optionally comprises a surface active agent (surfactant). Suitable surfactants include without limitation water-soluble salts of $C_8$-$C_{20}$ alkyl sulfates, sulfonated monoglycerides of $C_8$-$C_{20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

An embodiment of the composition optionally comprises a thickener. Any orally acceptable thickening agent can be used, including without limitation carbomers, also known as carboxyvinyl polymers, carrageenans, also known as Irish moss and more particularly—carrageenan (iota-carrageenan), high molecular weight polyethylene glycols (such as Carbowax®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

An embodiment of the composition optionally comprises flavorants, sweeteners, colorants, foam modulators, mouth-feel agents and others additively may be included if desired, in the composition.

An embodiment of the composition optionally comprises one or more further active material(s), which is operable for the prevention or treatment of a condition or disorder of hard or soft tissue of the oral cavity, the prevention or treatment of a physiological disorder or condition, or to provide a cosmetic benefit. Examples of such further active ingredient comprise a sialagogue or saliva-stimulating agent, an anti-plaque agent, an anti-inflammatory agent, and/or a desensitizing agent.

Adhesion enhancing agents can also be added to the oral care compositions which include but is not limited to waxes, inclusive of bees' wax, mineral oil, plastigel, (a blend of mineral oil and polyethylene), petrolatum, white petrolatum, shellac, versagel (blend of liquid paraffin, butene/ethylene/styrene hydrogenated copolymer) polyethylene waxes, microcrystalline waxes, polyisobutene, polyvinyl pyrrolidone/vinyl acetate copolymers, and insoluble polyacrylate copolymers.

Also effective as adhesion enhancing agents are liquid hydrophilic polymers including polyethylene glycols, nonionic polymers of ethylene oxide having the general formula: $HOCH_2(CH_2OCH_2)_{n1}CH_2OH$ wherein n1 represents the average number of oxyethylene groups. Polyethylene glycols available from Dow Chemical are designated by a number such as 200, 300, 400, 600, 2000 which represents the approximate average molecular weight of the polymer, as well as nonionic block copolymer of ethylene oxide and propylene oxide of the formula: $HO(C_2H_4O)_{a1}(C_3H_6O)_{b1}(C_2H_4O)_{c1}H$. The block copolymer is preferably chosen (with respect to a1, b1 and c1) such that the ethylene oxide constituent comprises from about 65 to about 75% by weight, of the copolymer molecule and the copolymer has an average molecular weight of from about 2,000 to about 15,000 with the copolymer being present in the liquid tooth whitening composition in such concentration that the composition is liquid at room temperatures.

A particularly desirable block copolymer for use in the practice of the present invention is available commercially from BASF and designated Pluraflo L1220 (PEG/PPG 116/66) which has an average molecular weight of about 9,800. The hydrophilic poly(ethylene oxide) block averages about 65% by weight of the polymer.

Synthetic anionic polycarboxylates may also be used in the oral compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 most preferably about 30,000 to about 700,000. Examples of these copolymers are available from GAF Corporation under the trade name GANTREZ® (methylvinylether/maleic anhydride), e.g., AN 139 (M.W. 500,000), AN 119 (M.W. 250,000); S-97 Pharmaceutical Grade (M.W. 700,000), AN 169 (M.W. 1,200,000-1,800,000), and AN 179 (M.W. above 1,800,000); wherein the preferred copolymer is S-97 Pharmaceutical Grade (M.W. 700,000).

When present, the anionic polycarboxylates is employed in amounts effective to achieve the desired enhancement of the efficacy of any antibacterial, antitartar or other active agent within the oral composition. Generally, the anionic polycarboxylates is present within the oral composition from about 0.05% to about 4% by weight, preferably from about 0.5% to about 2.5% by weight.

Adhesion enhancing agents employed in compositions of various embodiments of the invention are present in an amount of from about 0 to about 20% by weight. Preferably, the adhesion enhancing agents are present in an amount of from about 2 to about 15% by weight.

An embodiment of the composition optionally comprises a whitening agent which includes, but is not limited to peroxide compounds such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof.

In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite, pigments or dyes. In some embodiments the whitening agent is separated from the aqueous carrier. In some embodiments the whitening agent is separated from the aqueous carrier by encapsulation of the whitening agent.

In an additional aspect, the present invention provides a process for making the core shell silica particles as defined above comprising admixing an amount of silica particles in water with an amount of a base, wherein the base comprises a group I metal ion, to produce the core shell silica particles.

The base is not especially limited, provided it comprises a group I metal ion. The base is typically a strong base. Preferably the base is selected from the group consisting of sodium hydroxide, potassium hydroxide, sodium carbonate, potassium carbonate, trisodium phosphate, disodium phosphate, potassium phosphate, dipotassium phosphate, tetrasodium pyrophosphate, and tetrapotassium pyrophosphate. The base may have a pKb value in the range 0.1 to 3. For example sodium hydroxide has a pKb of 0.2, and potassium hydroxide has a pKb of 0.5.

In one embodiment of the composition, the composition comprises about 65%-99.9% of the carrier and further included ingredients, i.e. one or more of anti-caries agents, desensitizing agents, viscosity modifiers, diluents, surfactants, emulsifiers, foam modulators, pH modifying agents, abrasives, mouth feel agents, sweetening agents, flavor agents, colorants, preservatives, amino acids, anti-oxidants, anti-calculus agents, a source of fluoride ions, thickeners, an active agent for prevention or treatment of a condition or disorder of hard or soft tissue of the oral cavity, a whitening agent and combinations thereof. In another embodiment of the composition, the composition comprises about 80%-99.5% of the carrier and further included ingredients. In another embodiment of the composition, the composition comprises about 90%-99% of the carrier and further included ingredients.

The description of the optional ingredients above is also intended to include any combination of ingredients.

Components for Forming CSS Particles

As mentioned above, the silica is preferably selected from the group consisting of a precipitated silica, a fumed silica and a fused silica. The silica may be synthetic amorphous precipitated silica, such as Zeodent® 114 or Zeodent® 165 (J. M. Huber Corp), Absil 100 C or MFIL P (Madhu Silica). The silica may be a fumed silica, such as Aerosil 200 (Evonik). In another embodiment, the silica is a fused silica, which includes but is not limited to CAB-O-SIL® HP-60, produced by Cabot Corporation, TECO-SIL® 10 and TECO-SIL® 44css, produced by C-E Minerals, and Spheron P1500 made by the Japanese Glass Co.

Suitable silicas for use in the invention also include colloidal silicas (thickening silicas) having, such as the aerogels Syloid 244 and 266 (available from W. R. Grace Company), Aerosil (available from DeGussa Co.) and pyrogenic silicas sold under the tradename Cab-O-Sils (available from Cabot Corporation). Tixosil 333 and Tixosil 43B (available from Rhodia Ltda.), Zeodent 165 (available from J. M. Huber Corporation).

Other suitable silicas for use in the invention include silica abrasives which in turn include silica gels and precipitated amorphous silicas. These silicas are colloidal particles/particulates having an average particle size ranging from about 3 microns to about 12 microns, and more preferably between about 5 to about 10 microns and a pH range from 4 to 10 preferably 6 to 9 when measured as a 5% by weight slurry. Illustrative of silica abrasives useful in the practice of the present invention are marketed under the trade designation Sylodent XWA by Davison Chemical Division of W.R. Grace & Co., Baltimore, Md. 21203. Sylodent 650 XWA, a silica hydrogel composed of particulates of colloidal silica having a water content of 29% by weight averaging from about 7 to about 10 microns in diameter.

Other types of silica abrasives suitable for use in the invention include precipitated silicas having a mean particle size of up to about 20 microns, such as Zeodent 115, marketed by J.M. Huber Chemicals Division, Havre de Grace, Md. 21078, or Sylodent 783 marketed by Davison Chemical Division of W.R. Grace & Company.

The process may be carried out at a temperature in the range of from 17° C. to 90° C. In one embodiment the process is carried out at room temperature, i.e. 20 to 26° C. In another embodiment the process is carried out at a temperature of from 70 to 90° C. When preparing the core shell silica particles on an industrial scale, the mixer used to mix the reactants, such as a Lee mixer (Lee Industries), is preferably not heated up.

In one embodiment the base is sodium hydroxide and the process is carried out at a temperature of from 70 to 90° C. Preferably the temperature is from 80 to 90° C. Preferably, the base is 50% aqueous sodium hydroxide solution.

In another embodiment the base is potassium hydroxide. When using potassium hydroxide the process may be carried out at room temperature. The use of potassium hydroxide is preferred because the higher reactivity of potassium hydroxide (as compared to sodium hydroxide) means that the need for heating is avoided, and the reaction can be carried out at room temperature. Room temperature. Room temperature, sometimes referred to as ambient temperature is typically from 20 to 26° C., and is the temperature achieved when no external heating of the reaction mixture is used. When preparing the core shell silica particles on an industrial scale, the mixer used to mix the reactants, such as a Lee mixer (Lee Industries), cannot typically be heated up.

The reaction is:

$$2KOH + SiO_2 \Rightarrow K_2SiO_3 + H_2O$$

Typically, the formation of the core shell silica particles is complete after a time period of 2 hrs.

The weight ratio of the amount of base (for example, 50% aqueous NaOH solution) to the amount of silica particles is typically from 1:1 to 1:20. In a preferred embodiment, the weight ratio for the amount of base (for example 50% NaOH) to the amount of silica particles is from 1:1 to 1:6, optionally about 1:4. In one typical example 20% high cleaning silica and 4.5% NaOH (50%) were used, and the ratio is 4.5%:20%=1:4.44). This ratio may be used for toothpaste compositions.

Typically, the turbidity of the core shell silica particles is reduced by increasing the weight ratio for the amount of base to the amount of silica particles. For transparent core-shell silica (CSS) the weight ratio for the amount of base (for example 50% NaOH) to the amount of silica particles is greater than 0.5:1 and all of the silica particles have been dissolved. For translucent CSS particles the weight ratio of 50% NaOH to silica is from 0.45 to 0.49. For semi-opaque and opaque CSS particles the weight ratio of 50% NaOH to silica is from 0.20 to 0.45. For typical CSS toothpaste compositions, a ratio of 1:4.44=0.225:1 is used.

In a preferred embodiment, the reaction of the silica particles with the base causes a reduction in the d(0.5) value of the silica particles of from 1 to 15 nm to form the silica core, and $M_2SiO_3 \cdot xH_2O$ is formed on top of the silica core. Typically, there is a greater reduction in the d(0.5) value of the silica particles as the weight ratio for the amount of base to the amount of silica particles increases (see Table 1).

TABLE 1

| $SiO_2$/50% NaOH weight ratio V2 X | Volume change 2.02 $\Delta V/V$ | How much etched away $\Delta Y$ (nm) |
|---|---|---|
| 20 | −10.100% | −1.31 |
| 18 | −11.222% | −1.46 |
| 16 | −12.625% | −1.64 |
| 14 | −14.429% | −1.87 |
| 12 | −16.833% | −2.19 |
| 10 | −20.200% | −2.62 |
| 9 | −22.444% | −2.91 |
| 8 | −25.250% | −3.28 |
| 7 | −28.857% | −3.75 |
| 6 | −33.667% | −4.37 |
| 5 | −40.400% | −5.25 |
| 4 | −50.500% | −6.56 |
| 3 | −67.333% | −8.74 |
| 2.02 | −100.000% | −12.99 |
| Toothpaste 4.44 | −45.45% | −5.91 |

The reduction in the d(0.5) value of the silica particles of may be from 1 nm to 6 nm. The amount of silica etched away depends on the BET specific area of the silica particles. Particles with a greater surface area, e.g. porous particles like amorphous dental silica abrasives: high cleaning silica Zeodent 105; regular silica like Zeodent 114, thickening silica like Zeodent 165 will be etched less deep. Rigid silica particles will have a greater depth of etching.

As the covalent bonds of the $SiO_2$ network are turned into ionic bonds between $Na^+$ and $SiO_3^{2-}$, the surface becomes polarized and adsorbs water and the humectant to produce the core shell silica particle. As the reaction proceeds, the core shell silica particles can also become less transparent and more opaque, and the pH of the reaction solution decreases.

The weight ratio for the amount of humectant to water may be selected from a group of ratios consisting of 4:1 to 1:4; 3:1 to 1:3; 2:1 to 1:2; and 5:3 to 3:5.

In one embodiment, the d(0.5) value of the core shell silica particles formed by the process is at least 5% greater than the d(0.5) value of the silica starting material. It will be noted that although the diameter of the silica particle decreases during the process, forming a smaller silica core, the diameter of the whole CSS particle including the silicate layer is often greater than that of the original silica particle.

The formation of the core shell particles can be monitored by determining the pH of the reaction mixture. Core shell silica particles are formed when the pH of the reaction mixture decreases by at least 0.5 pH units from the initial mixture of reactants. Typically, the core shell silica particles are formed when the pH of the reaction mixture decreases by at least 0.8 pH units from the initial mixture of reactants. In another embodiment, the end point of the process results when pH of the reaction mixture decreases by at least 0.8-1.5 pH units from the initial mixture of reactants and does not exhibit any further decrease in pH. The formation of the core shell silica particles is usually complete when the pH is about 11.

The formation of the core shell particles can also be monitored by determining the conductivity of the reaction mixture. The end point of the process results when the conductivity of the reaction mixture decreases by at least 250 micro Siemens/cm (μS/cm) because the electric charges transfer from highly mobile ions (NaOH) to much less mobile silica surface (mobility≈0). In yet another embodiment, the end point of the process results when the conductivity of the reaction mixture decreases by 250-400 μS/cm. Typically, the core shell silica particles are formed when the conductivity of the reaction mixture decreases by at least 2 milli Siemens/cm (mS/cm). Usually, the core shell silica particles are formed when the conductivity of the reaction mixture decreases by at least 5 mS/cm.

Fumed Silica

Pyrogenic silica (sometimes called fumed silica or silica fume) is a very fine particulate or colloidal form of silicon dioxide. It is prepared by burning $SiCl_4$ in an oxygen rich hydrocarbon flame to produce a "smoke" of $SiO_2$. The silica particles fuse with one another to form branched, three-dimensional chain-like aggregates.

$$SiCl_4 + 2H_2 + O_2 \rightarrow SiO_2 + 4HCl.$$

Precipitated Silica

Amorphous silica, silica gel, is produced by the acidification of solutions of sodium silicate. An initially formed gelatinous precipitate is then washed and then dehydrated to produce colorless microporous silica. Idealized equation involving a trisilicate and sulfuric acid is shown:

$$Na_2Si_3O_7 + H_2SO_4 \rightarrow 3SiO_2 + Na_2SO_4 + H_2O$$

In the majority of silicates, the Si atom shows tetrahedral coordination, with 4 oxygen atoms surrounding a central Si atom. The most common example is seen in the quartz crystalline form of silica $SiO_2$. In each of the most thermodynamically stable crystalline forms of silica, on average, all 4 of the vertices (or oxygen atoms) of the $SiO_4$ tetrahedra are shared with others, yielding the net chemical formula: $SiO_2$. $SiO_2$ has a number of distinct crystalline forms (polymorphs) in addition to amorphous forms. With the exception of stishovite and fibrous silica, all of the crystalline forms involve tetrahedral $SiO_4$ units linked together by shared vertices in different arrangements.

Sodium Silicate

Sodium silicate is the common name for compounds with the formula $Na_2(SiO_2)_nO$. A well-known member of this series is sodium metasilicate, $Na_2SiO_3$. Also known as waterglass or liquid glass, these materials are available in aqueous solution and in solid form. Sodium carbonate and silicon dioxide react when molten to form sodium silicate and carbon dioxide:

$$Na_2CO_3 + SiO_2 \rightarrow Na_2SiO_3 + CO_2$$

Anhydrous sodium silicate contains a chain polymeric anion composed of corner shared $\{SiO_4\}$ tetrahedral, and not a discrete $SiO_3^{2-}$ ion. In addition to the anhydrous form, there are hydrates with the formula $Na_2SiO_3 \cdot nH_2O$ (where n=5, 6, 8, 9) which contain the discrete, approximately tetrahedral anion $SiO_2(OH)_2^{2-}$ with water of hydration. For example, the commercially available sodium silicate pentahydrate $Na_2SiO_3 \cdot 5H_2O$ is formulated as $Na_2SiO_2(OH)_2 \cdot 4H_2O$ and the nonahydrate $Na_2SiO_3 \cdot 9H_2O$ is formulated as $Na_2SiO_2(OH)_2 \cdot 8H_2O$.

In industry, the various grades of sodium silicate are characterized by their $SiO_2:Na_2O$ weight ratio (weight ratios can be converted to molar ratios by multiplication with 1.032), which can vary between 2:1 and 3.75:1. Grades with this ratio below 2.85:1 are termed 'alkaline'. Those with a higher $SiO_2:Na_2O$ ratio are described as 'neutral'.

In another embodiment, the silica is a precipitated silica, which includes, but is not limited to Zeodent® 114 and Zeodent® 165 (precipitated silica particles produced by J.M. Huber—chemical name: synthetic amorphous silica), Sylodent® 783 produced by W.R. Grace, Sorbosil® AC-43 produced by Ineos (PQ Corp.)

In another embodiment, the silica is a fused silica, which includes but is not limited to CAB-O-SIL® HP-60, produced by Cabot Corporation, TECO-SIL® 10 and TECO-SIL® 44css, produced by C-E Minerals, and Spheron P1500 made by the Japanese Glass Co.

In one embodiment, sodium hydroxide reacts with the surface of the $SiO_2$ particle to etch a shell of layers(s) of $Na_2SiO_3$ as follows:

$$SiO_2 + 2NaOH \rightarrow Na_2SiO_3 + H_2O$$

As can be seen from the reaction scheme, no NaOH will result in no change to the silica, whereas at the other extreme, complete reaction with 2 moles of NaOH per 1 mole of silica will result in the complete conversion into $Na_2SiO_3$. In order, to obtain the core shell particles of the invention, the reaction process must be controlled so as to not achieve particles comprising the appropriate proportion of $Na_2SiO_3$.

The core shell silica have adhesive properties when partially dried, for example, by air-drying because hydrated $Na_2SiO_3$ is adhesive (water glass).

In an embodiment, the core shell silica particles of the invention are formed when at least 1-6% of each of the silica particle starting material has been etched with one or more monolayers of $Na_2SiO_3$. In another embodiment, the core shell silica particles of the invention are formed when at least 2.5-5% of each of the silica particle starting material has been etched with one or more layers of $Na_2SiO_3$. In another embodiment, the core shell silica particles of the invention are formed when at least 3.5-4% of each of the silica particle starting material has been etched with one or more layers of $Na_2SiO_3$.

The formation of the core shell silica particles of the invention described above can be effected by manipulating the amount and type of base used, the amount of silica used, the amount of humectant used and varying the temperature of the reaction.

In an embodiment, the process further comprises admixing silica particles and base with a humectant. In an embodiment, the process further comprises the weight ratio of the amount of humectant to the amount of water being between from 4:1 to 1:4. In an embodiment, the process further comprises the weight ratio of the amount of humectant to the amount of water being from 3:1 to 1:3; from 2:1 to 1:2; or from 5:3 to 3:5. In an embodiment, the humectant comprises a mixture of two or more individual humectants. In an embodiment, the process further comprises a step of drying the product produced so as to remove a portion of the $H_2O$.

In an embodiment, the process further comprises reacting the amount of $SiO_2$ particles with the amount of NaOH and humectant at 50° C. to 140° C. In an embodiment, the process further comprises reacting the amount of $SiO_2$ particles with the amount of NaOH at 70° C. to 100° C. In an embodiment, the process further comprises reacting the amount of $SiO_2$ particles with the amount of NaOH at 70° C. to 90° C. In an embodiment, the process further comprises reacting the amount of $SiO_2$ particles with the amount of NaOH at 70° C. to 80° C. In an embodiment, the process further comprises reacting the amount of $SiO_2$ particles with the amount of NaOH at 74° C. to 76° C. In an embodiment, the process further comprises reacting the amount of $SiO_2$ particles with the amount of NaOH at 75° C.

In general, the use of a humectant in the reaction process allows for the use of higher temperatures within the ranges described above.

One of ordinary skill in the art can determine when the core shell silica particles of the invention have been obtained by several means in addition to sampling the reaction mixture and the test the core shell silica particles formed until CSS particles with the requisite properties in terms of layer formation and charge density have been formed.

In an embodiment, the end point of the process results when the average particle diameter of the core shell silica particle formed by the process is at least 5% greater in diameter than the average particle diameter of the silica ($SiO_2$) starting material. In another embodiment, the core shell silica particle is from 5%-10% greater in diameter than the average particle diameter of the silica starting material.

In an embodiment, the process further comprises admixing the core shell silica particle produced with a carrier to make a composition. In an embodiment, the process further comprises adjusting the pH of the composition to achieve a value of 7-9 pH adjustment can be achieved using an acid or base as necessary. In an embodiment, the pH adjustment is achieved using an acid.

In an additional aspect, the present invention provides a core shell silica particle obtainable by a process defined above.

In a further aspect, the present invention provides a method of reducing or inhibiting bacteria in the oral cavity which comprises applying the oral care composition defined above to a patient in need thereof to the oral surfaces of the patient.

In a final aspect, the present invention provides an ex vivo method of reducing or inhibiting bacterial in a patient's removable oral device which comprises applying the oral care composition described above to the surface of the removable oral device. Preferably the removable oral device is a denture, tray, mouthpiece, orthodontial braces and a retainer.

Another embodiment of the invention is a method of using the core shell silica particle for reducing or inhibiting bacteria in the oral cavity of a patient in need thereof, which comprises applying to the oral surfaces of the patient the composition of the invention.

Another embodiment of the method for reducing or inhibiting bacteria comprises applying the core shell silica particles ex vivo to a patient in need thereof, to the patient's removable oral device. In the context of the invention, the removable oral device includes, but is not limited to dentures, trays, mouthpieces, orthodontial braces and a retainer.

In one embodiment of the method, the patient is a mammal, which includes, but is not limited to humans and animals (e.g. dogs, cats, horses, cattle, sheep, llamas, etc.)

Another embodiment of the invention is the use of the core shell silica particle to make a composition for reducing or inhibiting bacteria in the oral cavity of a patient in need thereof, which comprises applying to the oral surfaces of the patient the composition of the invention or for reducing or inhibiting bacteria comprises applying the core shell silica particles ex vivo to a patient in need thereof, to a patient's removable oral device.

Embodiments of the present invention are further described in the following examples. The examples are merely illustrative and do not in any way limit the scope of the invention as described and claimed.

EXAMPLES

Example 1

The composition shown in Table 2 was used to produce the core shell silica particles. Zeodent® 114 and Zeodent® 165 are precipitated silica particles produced by J.M. Huber (chemical name: synthetic amorphous silica).

TABLE 2

Ingredients used in Example 1.

| Ingredients | weight in grams |
| --- | --- |
| Sorbitol | 361.3 |
| Water | 43.8 |
| Zeodent ® 114 | 40.8 |
| Zeodent ® 165 | 40.2 |
| Solid NaOH | 4.0 |

Example 2

The core shell particles of the present invention were compared with other silica based particles. The compositions used are shown in Table 3.

TABLE 3

Ingredients used in Example 2

| | Weight in grams | | |
| --- | --- | --- | --- |
| Ingredient | Control #1 | Control #2 | Example 2 |
| Sorbitol | 0 | 360 | 360 |
| Water | 483 | 43 | 43 |
| Zeodent ® 114 | 80 | 80 | 80 |
| 50% NaOH | 0 | 0 | 8 |
| Solid NaOH | 4 | 0 | 0 |

Without wishing to be bound by theory, it was believed that the particles produced in Control #1 did not have adhesive properties due to the lack of humectant (e.g., sorbitol) to keep the water on the silica particles, a preferred condition to ionize $SiO_2$.

Without wishing to be bound by theory, the particles produced in Control #2 also did not have adhesive properties because there was no NaOH to convert some of the $SiO_2$ into layers of $Na_2SiO_3$ covering the remaining $SiO_2$ core. In contrast, the core shell silica particles produced in Example 2 had adhesive properties similar to that of Example 1 above. These comparisons show that NaOH is needed, and water and/or humectant is/are preferable to obtain the core shell particles of the invention.

Example 3

In another comparative example, glycerin was substituted for sorbitol as the humectant component, and in two different weight ratios to water. The compositions prepared are shown in Table 4. Control #3 is similar to Example 1, but uses glycerin instead of sorbitol as the humectant and 8 g of 50% NaOH instead of 4 g of solid NaOH.

TABLE 4

Ingredients and Respective Weights Used in Control #3 and Example 3.

| | Weight in grams | |
|---|---|---|
| Ingredient | Control #3 | Example 3 |
| Glycerin | 361.3 | 252 |
| Water | 43.8 | 151 |
| Zeodent ® 114 | 40.8 | 80 |
| Zeodent ® 165 | 40.2 | 0 |
| 50% NaOH | 8 | 8 |

Without wishing to be bound by theory, the particles produced in Control #3 did not have adhesive properties likely because there was an insufficient amount of water to convert $SiO_2$ into $Na_2SiO_3$. In contrast, the core shell silica particles produced in Example 3 had adhesive properties.

Example 4

React $SiO_2$ abrasives with NaOH solution to create core-shell particles.

The reaction is: $2NaOH + SiO_2 \Rightarrow Na_2SiO_3 + H_2O$ 0.8% NaOH (50% solution) was used in clear silica colloids (see Table 5). When NaOH reacts with excess $SiO_2$, the pH will go beyond 11, then comes down gradually to below 10.0 (for toothpaste application, it requires the pH range between 6 and 10). The transition time is 6-24 hours at room temperature, but it may be much shorter by heating to higher temperature such as 75° C. The optical properties of the colloids change during the reaction, from transparent to opaque.

Table 5 making core-shell silica colloids (model colloids)

| Core-shell silica colloids | amount in grams | Control | amount in grams |
|---|---|---|---|
| Sorbitol | 359.8 | Sorbitol | 359.8 |
| Water | 43.2 | Water | 43.2 |
| Zeodent 114 | 80 | Zeodent 114 | 80 |
| mix for 30 minutes, clear colloids | | mix for 30 minutes, clear colloids | |
| 50% NaOH | 8 | | |
| Mix for several hours at room temperature, becomes semi-opaque | | | |

The optical appearance changes because the refractive index is changed on the shell. This makes sense because $SiO_2$ is known to be able to react with NaOH (or $Na_2CO_3$ or other strong bases) forming $Na_2SiO_3$, and the refractive index matched to $SiO_2$ (1.44-1.45) becomes mis-matched so the transparency is gone.

The present inventors postulated that the product of $NaOH + SiO_2$ is hydrated $Na_2SiO_3$ (refractive index is lower than $SiO_2$, or $n_D < 1.44$). To confirm this hypothesis, a higher refractive index non-crystallizing sorbitol (refractive index=1.455-1.465) was used to increase the refractive index of aqueous solution (surrounding silica particles) to match the refractive index of core shell silica. It does turn back into completely transparent colloids. This simple experiment evidences that the shell consists of low refractive index hydrated $Na_2SiO_3$ which is attached on the silica core. The inventors found a physical model for concentric rigid non-porous spherical particle light scattering to explain why colloids become opaque from transparent reactants.

Example 5

Physical Model for Core-Shell (Concentric) Particles Light Scattering

This model is based on "light Scattering by Small Particles", H. C. van de Hulst, 2003, pages 67-77.

The scattering intensity is proportional to the dielectric constant, $\alpha$.

For simple spherical particles:

$$\alpha = \frac{m^2 - 1}{m^2 + 2} \times a^3$$

Where:
m=np/nm, where np and nm are the refractive indices of particle and water aqueous medium surrounding the particles (water+sorbitol+salts)
a is the particle radius For a concentric particle as shown in FIG. 1B:
For the core particle, n1 is the refractive index, qa is the radius (q is the ratio of radius between core and shell).
For the shell, n2 is the refractive index, a is the radius
Where the refractive index (n) are defined as below:
n=n1 for 0<r<qa
n=n2 for qa<r<a
n=1 for r>a (air for this case)
The dielectric constant for such core-shell (concentric) particle is: (depends on only 4 parameters only: n1, n2, and q, a)

$$\alpha = a^3 \times \frac{(n_2^2 - 1) \times (n_1^2 + 2n_2^2) + q^3(2n_2^2 + 1) \times (n_1^2 - n_2^2)}{(n_2^2 + 2) \times (n_1^2 + 2n_2^2) + q^3(2n_2^2 - 2) \times (n_1^2 - n_2^2)}$$

We can see the dielectric constant or light scattering intensity is different for simple spherical and concentric particles.

Example 6

Plurality of monolayers: Calculations via ESCA, titration data, Raman spectroscopy and mass indicate that the particle's shell comprises multiple monolayers of sodium silicates. Values of 2, 4, 16, 32 and 36 shell monolayers were obtained.

ESCA Analysis of Core Shell Silica (CSS) Powder

ESCA (Electron Spectroscopy for Chemical Analysis) was used to determine the surface composition of CSS powder, prepared in aqueous media from $SiO_2$ and NaOH. ESCA only analyzes the outer 10 nm of the sample surface, so it the ideal method for detection of silicate on the surface of the silica powder. The samples analyzed included the as dried powder as well as that briefly rinsed three times with deionized water to remove any soluble residues from the surface. The ESCA surface composition data for the CSS powders are shown in Table 6.

TABLE 6

ESCA Analysis of Core Shell Silica (CSS) particles from $SiO_2$ (Zeodent 105).

| | Atomic percent | | | |
|---|---|---|---|---|
| | $O_{total}$ | Si | $O_{SiO3}$ (O*) | Na |
| $SiO_2$ (Zeodent 105) | 69.30 | 30.30 | 0.00 | 0.41 |
| Na-CSS (as dried) | 65.17 | 29.53 | 2.22 | 3.13 |
| 3x $H_2O$ rinse | 65.94 | 29.24 | 1.94 | 2.52 |

The data reveal that a significant increase in sodium has occurred on the surface of the as dried material, relative to that for silica. In addition, a low intensity oxygen peak that is characteristic of silicate ($O_{SiO3}$) was also observed in the data. This peak is not observed for $SiO_2$. The detection of Na and the silicate oxygen peak strongly support the formation of sodium silicate on the surface of the silica powder. Rinsing the as dried CSS powder with deionized water reduces the Na and silicate oxygen slightly, indicating that the surface silicate has low water solubility. Thus the sodium silicate is largely retained on the silica surface in aqueous media.

CSS powders that had been subjected to 1% $CaCl_2$ solution were also studied by ESCA to determine Ca uptake by the material. The ESCA results for the as dried material clearly indicate the presence of Ca on the surface of the CSS. A reduction in Na was also observed relative to the as dried CSS, suggesting that Ca substitutes for Na on the CSS surface. A low concentration of Cl was also detected for the $CaCl_2$ treated sample suggesting residual $CaCl_2$ may also be present on the material. Deionized water rinsing of the sample removed the Cl, however most of the Ca was retained. Thus the data indicate that the CSS is able to adsorb and retain Ca ions from aqueous solution. This result supports the Ca ion uptake data described above, and supports the potential for CSS to act as a tartar control agent.

Example 7

Mid IR and Polarization Analysis

Mid IR spectroscopy was used to confirm the presence of silicate present on the shell layer of core silica. In all of the measurements, a three (multi) reflection ATR (Attenuated Total Reflectance) accessory was used to enhance the absorption spectrum from the samples. These accessories only allow light to penetrate 1-2 microns into the sample thus enhancing the signal from surface components compare with the bulk matrix. To further enhance the signal to noise, 32 scans were measured and averaged for each measurement.

The Mid IR fingerprint of silica and silicate are quite different and well resolved. Pure silica is characteristic of having a symmetric SiO vibration near 1074 cm-1 and a band around 960 $cm^{-1}$ due to the stretching vibration of SiOH bonds. Silicates, on the other hand, have a prominent asymmetric shoulder vibration between 1200 $cm^{-1}$ and 1100 $cm^{-1}$. In addition, a strong asymmetric stretch, shifted from silica is found near 1000 $cm^{-1}$.

The ATR spectral fingerprint of Core Shell Silica Paste is greatly influenced by refractive index effects which can be large for inherently strong absorptions like Si—O stretching in silica and silicates. In transmission the Si—O band is near 1100 $cm^{-1}$ but in ATR it is typically around 1060 $cm^{-1}$. Also the bands are not totally symmetrical. Because these are pastes absorption is broad and potentially contains both amorphous/crystalline material.

In addition to regular ATR measurements, a Polarization Accessory was added to enhance our understanding and confirmation that a surface silicate species was present. The benefit of polarization measurement is that they give additional information on the molecular structure of a sample as it pertains to the crystallinity or molecular orientation. In this application, as the plane of polarized light orients along the sample plane, the ratio of silica to silicate should change. The polarization angles tested were: 0, 30, 60, 90, 120, 150, and 180 degrees. The spectral ratio of silicate (1022 $cm^{-1}$) to silica (1074 $cm^{-1}$) were calculated to demonstrate presence of shell silicate. Table 7 shows the results from this analysis for Na-CSS.

TABLE 7

| Polarization Angle (degrees) | Ratio Silicate/Silica |
| --- | --- |
| 0 | 1.143 |
| 30 | 1.135 |
| 60 | 1.106 |
| 90 | 1.066 |
| 120 | 1.069 |
| 150 | 1.113 |
| 180 | 1.132 |

The analysis shows an optimal concentration of silicate at 0 degrees when the plane of polarized light is positioned suggesting that the dipole moment change of silicate is located horizontal to the ATR surface.

Example 8

Kinetics

A kinetic study was conducted to determine the time period required to make Na+-CSS colloids in situ. The following recipe was used based on a Na+-CSS toothpaste recipe (#85 CSS toothpaste).

TABLE 8

| Na+-CSS colloid recipe | |
| --- | --- |
| Ingredients | grams |
| Water | 1452 |
| Glycerin | 2018 |
| NaOH (50%) | 270 |
| Zeodent 105 | 1320 |

Procedure: add water, NaOH, and glycerin in a reaction container. Add Zeodent 105 high cleaning silica slowly into the aqueous mixture. Heat up the mixture using a steam water-bath to maintain the reaction temperature in the range of from 80-90° C. React for 6 hours. Take a sample out every 1 hour to measure pH and conductivity when cooled down to room temperature. The data is listed below:

TABLE 9

| Kinetic data | | |
| --- | --- | --- |
| time, hr | conductivityt (micro Siemen/cm) | pH |
| 0 | 5220 | 12.218 |
| 1 | 1880 | 11.420 |
| 2 | 1324 | 11.508 |
| 3 | 1248 | 11.526 |
| 4 | 1077 | 11.544 |
| 5 | 680 | 11.625 |
| 6 | 469 | 11.647 |

We can see from Table 9 that the pH and conductivity dramatically decrease in the first hour and then level out after 2 hours. The reaction to form CSS reaction finishes in approximately 2 hours. This kinetic study is important because it is necessary to minimize the toothpaste batch making time.

A potassium core shell silica (K-CSS) colloid based on the following recipe:

TABLE 10

K+-CSS colloid recipe

| Ingredient | Amount in grams |
|---|---|
| Water, 75° C. | 117 |
| Glycerin | 343 |
| 45% KOH | 101.1 |
| SiO$_2$ | 220 |

Procedure: add hot water (75° C.), 45% KOH, and glycerin in a reaction container. Add Zeodent 105 high cleaning silica slowly into the aqueous mixture. Let react for 6 hours at ambient temperature without additional heating. Take samples out during the reaction to measure temperature, pH and conductivity. The kinetic data is listed below:

TABLE 11

Kinetic data for K+-CSS colloidal sample

| time (min) | conductivity (μS/cm) | temperature (° C.) | pH |
|---|---|---|---|
| 0 | 9530 | 50.8 | |
| 3 | 7520 | 51.9 | |
| 4 | 6500 | 51.6 | |
| 13 | 4240 | 46.6 | 11.107 |
| 21 | 3730 | 42.8 | 11.552 |
| 35 | 3290 | 37.6 | 11.552 |
| 46 | 3080 | 36.1 | 11.552 |
| 59 | 2888 | 33.2 | 11.566 |
| 75 | 2689 | 31 | 11.597 |
| 85 | 2465 | 29.9 | 11.606 |
| 219 | 2291 | 25.7 | |
| 410 | 2211 | 23.2 | 11.59 |

Table 11 shows that the conductivity dramatically decreases in the first hour and then levels out after 2 hours. So the CSS reaction finishes after approximately 2 hours at ambient (room) temperature.

The above colloid recipe was changed to make a K-CSS toothpaste by decreasing the 45% KOH/SiO$_2$ from 101.1 g/220 g to 303.2 g/1321 g and did the kinetic measurement again:

TABLE 12

K+-CSS colloid recipe (decreased KOH:SiO$_2$ ratio)

| Ingredient | Amount in grams |
|---|---|
| Water, 75° C. | 1005 |
| Glycerin | 2029.3 |
| 45% KOH | 303.2 |
| SiO$_2$ | 1321 |

TABLE 13

Kinetic data for #118 colloidal sample

| time (min) | conductivity (μS/cm) | temperature (° C.) | pH |
|---|---|---|---|
| 0 | (before adding KOH) 934 | | 6.963 |
| 0 | (after adding KOH) 4530 | 49.6 | 11.66 |
| 1 | 3270 | 49.7 | |
| 2 | 3030 | 49 | |
| 3 | 2980 | 48.8 | |
| 4 | 2910 | 48.3 | |
| 5 | 2848 | 48 | 11.666 |
| 15 | 2684 | 44.6 | 11.568 |
| 29 | 2510 | 40.7 | 11.621 |
| 30 | 2462 | 40.9 | 11.572 |
| 40 | 2400 | 38.9 | 11.624 |
| 54 | 2282 | 36.7 | 11.634 |
| 79 | 2101 | 33 | 11.646 |
| 92 | 2021 | 32.2 | 11.627 |
| 109 | 1970 | 30.7 | 11.649 |
| 115 | 1924 | 30.6 | 11.645 |

From Table 13, we can see that the conductivity dramatically decreases in the first half hour and levels out after 2 hours. Thus, K-CSS colloids for K-CSS toothpaste can be made in approximately 2 hours at ambient temperature without any external heating (see K-CSS toothpaste in Table 14). This kinetic study is important because it is necessary to minimize the toothpaste batch making time.

TABLE 14

K-CSS toothpaste

| Ingredient | Amount in grams |
|---|---|
| Thickener | 0.2 |
| PEG 600 | 3 |
| Humectant | 37.305 |
| Sweetener | 0.5 |
| Fluoride source | 0.243 |
| H$_3$PO$_4$ | 2 |
| 45% KOH | 5 |
| | (2.25% KOH) |
| Zeodent 105 silica | 20 |
| Zeodent 165 silica | 4.5 |
| Surfactant | 2 |
| Flavor | 1.3 |
| Water | 23.7 |
| FD&C #1 - blue dye | 0.002 |
| TiO$_2$ coated mica | 0.25 |
| Total | 100 |

The K-CSS toothpaste had a pH of 7.7 and a 10% pH of 8.06 (10% pH is the pH for 10% toothpaste solution by adding 10 g toothpaste in 90 g water (10% pH should be between 6 and 10 for toothpaste). Note that 1 Brookfield viscosity unit is 10,000 centipoise.

ESCA spectroscopy was used to quantify the elements of K in the K-CSS particle.

TABLE 15

ESCA data for K and Zn (2.25% KOH/2% H$_3$PO$_4$) in K-CSS toothpaste

| | Atomic percent | | | | | |
|---|---|---|---|---|---|---|
| | C | O | Na | Si | P | K |
| 4x H$_2$O wash | 2.40 | 67.63 | 0.15 | 29.17 | 0.00 | 0.67 |
| 6x H$_2$O wash | 2.03 | 67.82 | 0.13 | 29.45 | 0.00 | 0.58 |

We can see from Table 15 that K is found on the CSS abrasive surface. In summary, KOH can be used as the base to make K-CSS toothpaste at room temperature.

Example 9

Process for Making K-CSS at Room Temperature

An example protocol for making K-CSS at room temperature is set out below:

Add pilot plant water at 75° C. to the lee mixer and then add glycerin. Add SiO2 (Zeodent 105). Add KOH. Mix ingredients. Remove samples at regular intervals and test pH and conductivity to determine when formation of K-CSS is complete. Add $H_3PO_4$—the reaction mixture forms a gel. Take sample out and add NaF, saccharin and water in the Lee mixer, and mix for 10 minutes. Disperse CMC/Xanthan gums in PEG 600 solution. Add the above gum solution in the Lee mixer. Mix. Slowly add Zeodent 165 thickening silica. Apply 25 inch vacuum for a period of time. Remove vacuum, and add flavor, dye, and mica. Turn on scraper and agitator, the color looks light blue, viscosity is quite thin before adding SLS. Mix for 10 min under vacuum. Stop vacuum/mixing. Add SLS. Apply vacuum, mix slowly, to form a product which has a thicker consistency but is still thin. The measured density of the final product is 1.279. The product has a light blue colour. The measured initial viscosity=156600 cp after 2 hrs sitting. Brookfield viscosity=150600 cp, barely flowable in a 1 Gal jar.

Example 10

Transparent CSS

React $SiO_2$ abrasives with NaOH solution to create core-shell particles at elevated temperature (70-90° C.). The reaction is:

$$2NaOH + nSiO_2 \Rightarrow Na_2O\text{-}nSiO_3 + H_2O \quad (1)$$

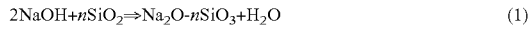

Previously, we made opaque toothpaste by reacting excess $SiO_2$ with NaOH ($SiO_2$:50% NaOH=20%: 4.5%=4.44:1 weight percent ratio). In this way, only a small portion (a surface) of the $SiO_2$ particle reacts with NaOH. It was not known how many percent of $SiO_2$ reacts with NaOH because the ratio of $SiO_2$ to NaOH is n:2 based on the above reaction (n is not known).

It was desirable to make transparent or translucent mouthwash products using CSS materials. It is necessary to know how much NaOH is needed to fully dissolve $SiO_2$ in order to make transparent CSS. We made transparent CSS colloids from the following recipe by minimizing the ratio of $SiO_2$ to 50% NaOH in order to achieve maximum particle charge density.

TABLE 16

| Transparent Na-CSS colloids | | |
|---|---|---|
| Ingredient | Amount in grams | moles |
| Water | 2847.4 | |
| Zeodent 105 | 280.1 | 4.662 |
| 50% NaOH | 234 | 2.925 |

The $SiO_2$ was fully dissolved in NaOH at 85 C for 4 hours, forming transparent liquid. When calculating their molar concentrations, the molar ratio of $SiO_2$ to NaOH (4.662 moles: 2.925 moles)=1.593:1 (molar ratio). However, if we assume the following reaction:

$$2NaOH + SiO_2 \Rightarrow Na_2SiO_3 + H_2O \quad (2)$$

$SiO_2$: NaOH=1:2 molar ratio, only 2.925 moles/2 of $SiO_2$ dissolves, or Dissolved $SiO_2$/total $SiO_2$=(2.925)/2 moles/ (4.662 moles)=0.3138. Thus, the majority of $SiO_2$ is not dissolved. This is contradictory to what we observed: all silica was apparently dissolved, forming transparent solution. This calculation indicates that reaction (2) is invalid and reaction (1) is more appropriate. If all silica dissolved, n>2×1.593=3.186.

To further confirm this finding, 37.5% $Na_2SiO_3$ commercially available from PQ Corp., was used as control sample in this study. For this commercial transparent Na2SiO3 liquid sample, $SiO_2$:$Na_2O$ weight ratio=3.220:1 or molar ratio=3.323:1. This is equivalent to $SiO_2$:NaOH=3.323: 2=1.662:1. $Na_2SiO_3$/total $SiO_2$=(½) moles/(1.662 moles)=30.08% Thus, for commercial $Na_2SiO_3$ solution, n>3.323.

The samples were analyzed by light scattering and ESCA to determine if there are some small nanometer particles in the transparent colloids. Based on the above recipe in Table 16, we fine-tuned the ratio of $SiO_2$ to 50% NaOH and made the following recipes:

TABLE 17

| Recipes for making opaque, translucent, and transparent Na-CSS colloids | | | | | | |
|---|---|---|---|---|---|---|
| batch# | #148 | #149 | #152 | #153 | #151 | #150 |
| Water (75° C.) | 2867 | 2834 | 2824 | 2825 | 2826 | 2866 |
| Zeodent 105 | 280 | 421 | 455 | 455 | 490 | 560 |
| 50% NaOH | 234 | 224 | 224 | 226.1 | 220 | 224 |
| Ratio of Silica to 50% NaOH | 1.197 | 1.880 | 2.028 | 2.012 | 2.227 | 2.497 |
| pH | 11.57 | 11.10 | 11.02 | 11.40 | 11.11 | 11.07 |
| appearance | transparent | transparent | translucent | translucent | semi-opaque | opaque |
| mean particle diameter, μm | 0 | 0 | 35.01 | 32.25 | 23.45 | 16.85 |

Figure 3:
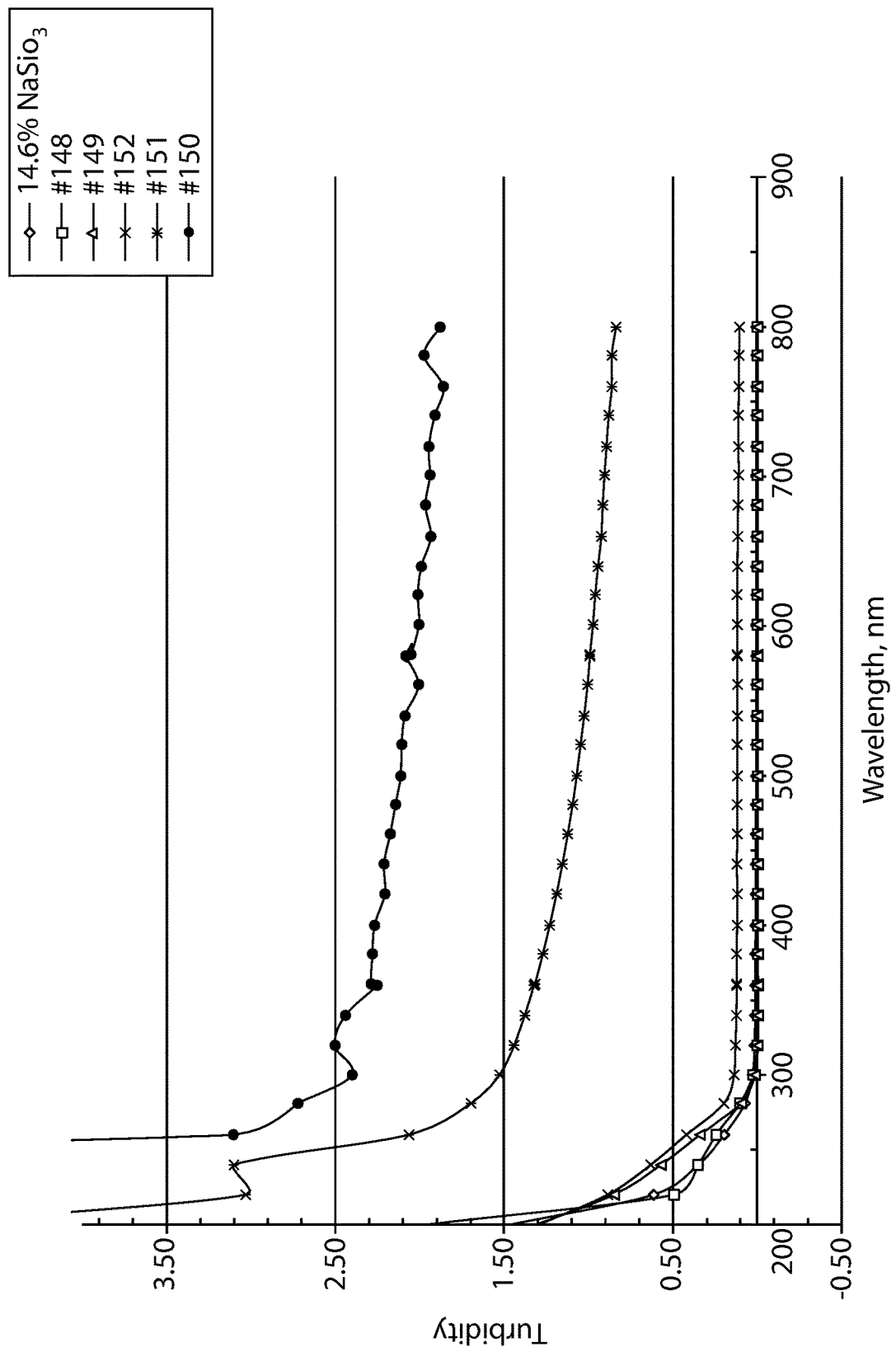
FIG. 3 shows a schematic of a core shell silica particle of the invention wherein an internal surface of the silica core is etched with metal silicate.

The translucent Na-CSS colloid was found when $SiO_2$ to 50% NaOH weight ratio=2.028:1 or molar ratio=2.700:1. So when n≤2.700×2=5.400, all silica will fully dissolve. UV-visible spectra were measured for the above 5 samples using a 0.20 mm thick quartz UV optical cell (see FIG. 3). 14.6% Na2SiO3 solution, prepared from 37.5% $Na_2SiO_3$ commercial product from PQ Corp., was used as control sample.

It is seen that the translucent (#152) and transparent (#148 and #149) colloids have similar turbidity spectra as the control sample: there is no scattering in the visible region between 300 and 800 nm probably because of the absence of $SiO_2$ particles or if silica particles are present they are very small, and some scattering or absorption in the UV region between 200 and 300 nm. As more silica is used in the formula, the semi-opaque (#151) and opaque (#150) samples show much higher scattering background from the $SiO_2$ particles in the visible and UV regions.

ESCA Analysis:

TABLE 18

ESCA Analysis of Na-CSS #152

| | Atomic Percent | | | | Atomic Ratio | | Peak Position (eV) |
|---|---|---|---|---|---|---|---|
| | $O_{total}$ | Si | $O_{SiO3}$ | Na | Si/O | Na/Si | Si |
| #152 Na-CSS | 67.92 | 29.56 | 1.69 | 2.53 | 0.44 | 0.09 | 103.3 |
| 37.5% $Na_2SiO_3$ | 63.56 | 23.25 | 11.73 | 13.20 | 0.37 | 0.57 | 102.8 |
| $SiO_2$ (Zeodent 114) | 68.97 | 30.67 | 0.00 | 0.36 | 0.44 | 0.01 | 103.4 |

Based on the above ESCA data, the translucent sample (#152) contains (based on Na data) $Na_2SiO_3\% = 37.5\% \times 2.53/13.20 = 7.19\%$. From the #152 recipe, if all NaOH reacts with silica, we get 6.84% $Na_2SiO_3$, which is very close to the value calculated from the above ESCA data (7.19%).

Table 19 below shows the particle size distributions for silica and CSS particles as determined by light scattering. Table 19 shows the particle size distribution for fumed silica, for an Na-CSS colloid, for Zeodent® 105 precipitated silica, for an opaque Na-CSS (#150), for a semi-opaque Na-CSS (#151), and for a translucent Na-CSS (#152).

TABLE 19

| Composition | d (0.1) | d (0.5) | d (0.9) | Span (10%-90%) |
|---|---|---|---|---|
| Fumed Silica | 20.08 μm | 45.96 μm | 92.75 μm | 1.581 |
| Zeodent 105 Silica | 2.80 μm | 10.31 μm | 34.44 μm | 3.069 |
| #153 NaCSS Colloid | 11.92 μm | 28.78 μm | 57.91 μm | 1.598 |
| # 150 Colloids Na-CSS | 4.62 μm | 12.73 μm | 34.67 μm | 2.361 |
| # 151 Colloids | 8.07 μm | 19.85 μm | 43.96 μm | 1.808 |
| # 152 Colloids | 12.03 μm | 31.29 μm | 63.50 μm | 1.645 |

The small particles may form bigger clusters due to the high surface area (energy). This was seen from the commercial fumed silica sample (mean particle diameter was reported to be 12 nm) which mean particle size was 51.90 μm by a light scattering method. SEM picture also revealed that fumed silica particles form bigger clusters. It is seen from the particle size distributions: (1) the size distribution after reaction with NaOH is narrower than the commercial Zeodent 105 high cleaning powder (control); (2) the smaller particles dissolve before the larger size portion.

One other means to distinguish etched CSS particles from completely formed metal silicate (e.g. $Na_2SiO_3$) is to compare viscosity. The 37.5% $Na_2SiO_3$ solidified at pH 11.3. When diluted nearly 10× to a 3.32% $Na_2SiO_3$, the solution still solidified at a pH of about 9. In contrast, the CSS particles of the invention remained in solution at these concentrations and pHs. As such, another embodiment of the invention is to form CSS particles which remain in a flowable colloidal form (i.e. non-solidified) over the entire 10% pH (pH for 10% toothpaste solution by adding 10 g toothpaste in 90 g water) range of pH 6-10 which is distinguishable from other completely formed metal silicates which would solidify at pHs of about greater than or equal to pH 9.

Example 11

Etching of Silica by NaOH

CSS can be made from any kind of silica materials, e.g. rigid silica particles, porous silica particles like amorphous dental silica abrasives: high cleaning silica Zeodent 105; regular silica like Zeodent 114, thickening silica like Zeodent 165.

The amount of silica etched away depends on the BET specific area of the silica particles—particles with a greater surface area will be etched less deep. The amount of etching also depends on the ratio of silica to base. It was found that when the weight ratio of Zeodent 105 silica vs 50% NaOH solution=2.02 (endpoint), all silica dissolves. When we make Na-CSS toothpaste, 20% high cleaning silica (Zeodent 105) and 4.5% of 50% NaOH were used. So the ratio of $SiO_2$:50% NaOH=4.44:1. Since dissolved $SiO_2$:50% NaOH=2.02:1, so the remaining SiO2 to NaOH (50%)= (4.44−2.02):1=2.42:1 after reaction. So the remaining SiO2 vs initial SiO2=2.42/4.44=54.55%, or volume change (ΔV/V)=54.55%−100%=−45.45%. Note the endpoint for dissolving all silica material might vary from $SiO_2$ to $SiO_2$ (different silicas may have different endpoints, so for example endpoint for fumed silica may not be 2.02:1).

Calculation from BET Specific Surface Area

Calculation for all $SiO_2$ (including both rigid and porous particles) uaing BET specific surface area (S/W). For high cleaning silica (e.g. Zeodent 105, S/W=35 $m^2/g$ and density d=2.2 $g/cm^3$), the change in particle diameter (ΔX) is given by the following formula:

$$\Delta X = [(\Delta V/V)/(S/W)] \times 1/d$$

$$\Delta X = (-0.4545/35 \times 10^4 \text{ cm}^2/\text{g}) \times (1/2.2 \text{ g/cm}^3)$$

$$\Delta X = -5.90 \times 10^{-7} \text{ cm}$$

$$\Delta X = -590 \text{ nm} (-0.590 \text{ μm})$$

Calculation from Particle Diameter

An alternative calculation is available for monodisperse, rigid, spherical particles. Since the particle outer surface area is very small (compared to microporous particles), the rigid particles will have a higher degree of etching.

Take the derivative:

$$V = \frac{1}{6}\pi D^3$$

$$dV = \frac{1}{2}\pi D^2 dD$$

$$\frac{dV}{V} = 3 \times \frac{dD}{D} =$$

$$\frac{dD}{D} = -\frac{1}{3} \times \frac{dV}{V}$$

For a 12 nm fumed silica (e.g. Aeorsil 200), if dV/V=−0.4545 by assuming the same relative volume change ratio as high cleaning silica (e.g. Zeodent 105), the change in particle diameter ΔD=−0.1515×12 nm=−1.8 nm. This change in diameter (−1.8 nm from a 12 nm silica) is proportionally greater than the high cleaning silica (−0.590 μm of a 10 μm silica=5.9%).

Example 12

Model for the Number of Layers of $Na_2SiO_3$ on Silica Surface Using ESCA Data

ESCA (Electron Sprectroscopy for Chemical Analysis—also known as XPS or X-ray Photelectron spectroscopy) can penetrate down from surface to 10 nm deep. 1 layer of Silica or $Na2SiO_3$ is ca. 1 Å (0.1 nm). For $Na_2SiO_3$ molecule: Na/Si=2:1. So for 100 monolayers, Na/Si=0.02:1. But from ESCA data: Na/Si=0.084:1 So there are 0.084/0.02=4.2≈4 layers of $Na_2SiO_3$.

Example 13

Model for the Number of Layers of $Na_2SiO_3$ on Silica Surface Using Raman Spectroscopy $$B1 = \frac{Na2SiO3 \text{ weight (g)}}{CSS \text{ colloid total weight (g)}} \times 100\% \text{ (determined by Raman Spectroscopy)}$$

$$B2 = \frac{Na2SiO3 \text{ weight (g)}}{CSS \text{ colloid volume (cm}^3)} = \frac{Na2SiO3 \text{ weight (g)}}{CSS \text{ colloid weight (g)}} \times \frac{CSS \text{ colloid weight (g)}}{CSS \text{ colloid volume (cm}^3)} = B1 \times CSS \text{ colloid density } (d)$$

$$B3 = \frac{Na2SiO3 \text{ weight (g)}}{\text{Silica surface (cm}^2)} = \frac{Na2SiO3 \text{ weight (g)}}{CSS \text{ colloid volume (cm}^3)} \times \frac{CSS \text{ colloid volume (cm}^3)}{\text{Silica surface (cm}^2)} \times \frac{\text{Silica volume (cm}^3)}{\text{Silica volume (cm}^3)}$$

where $$\frac{\text{Silica surface (cm}^2)}{\text{Silica volume (cm}^3)} = \frac{4\pi r^2}{\frac{4}{3}\pi r^3} = \frac{3}{r}$$

$$\frac{\text{Silica volume (cm}^3)}{CSS \text{ colloid volume (cm}^3)} =$$

silica volume % (Φ %) determined from CSS recipe $$B3 = B2 \times \frac{r}{3} \times \frac{1}{\Phi \%} = B1 \times d \times \frac{1}{3} \times \frac{r}{\Phi \%}$$

$$B4 = \frac{\text{\# of Na2SiO3 molecules}}{\text{Silica Surface area (cm}^2)} = \frac{B3}{Na2SiO3 \text{ M.W.}} \times 6.023 \times 10^{23}$$

$$B5 = Na2SiO3 \text{ surface coverage } (\theta)$$

$$= \frac{\text{\# of Na2SiO3 molecules}}{\text{\# of SiO2 molecules}}$$

$$= \frac{B4}{\left(\frac{(1 \text{ cm} \times 10^8 \text{ A/cm})^2}{\text{SiO2 molecule cross section area (A}^2)}\right)}$$

$$= \frac{B1 \times d \times \frac{1}{3} \times \frac{r}{\Phi \%} \times}{Na2SiO3 \text{ M.W.}}$$

$$\frac{6.023 \times 10^{23}}{\left(\frac{(1 \text{ cm} \times 10^8 \text{ A/cm})^2}{\text{SiO2 molecule cross section area (A}^2)}\right)}$$

$$= \frac{3.5\% \times 1.189 \times \frac{5 \times 10^{-4} \text{ cm}}{3 \times 8.13\%} \times}{122.06}$$

$$\frac{6.023 \times 10^{23}}{\left(\frac{(1 \text{ cm} \times 10^8 \text{ A/cm})^2}{0.762 \text{ A}^2}\right)}$$

= 32.1 layers

Example 14

Spray Dry Synthesis of CSS Particles

Synthesis Procedure:

Add water and 50% NaOH in a reaction container. Keep stirring with a mechanical stirrer (ca.200 RPM). Heat up the aqueous solution using 100° C. steam water-bath to control the temperature at 80-90° C. Add Zeodent 105 (high cleaning silica powder) into the solution slowly. Keep stirring. react for 4 hours to make Na+-CSS colloids at ca. 85° C. Stop heating and cool down to room temperature. Keep stirring overnight. Use filter paper to filter the above colloids with vacuum. Collect the filtered liquid. Wash the Na+-CSS wet solid using water to remove the soluble metal ions. Dry the Na+-CSS colloid to obtain dry Na-CSS abrasive by spray drying. Calculate yield (close to 100%), which yield was slightly over 100% because there were some water moisture in the solid without complete evaporation during drying.

Example 15

Freeze Dry Procedure

Alternatively, the filtered liquid of Example 14 is then mixed with DI water, the mass ratio between water and Na-CSS is about 1:1. Freeze the mixture until it becomes solid. Turn on the freeze drier to cool the chamber. When the temperature of the chamber drops down to −47° C., load the frozen sample into the chamber and turn on vacuum for a period of time sufficient to form dried CSS powder.

Example 16

The core shell silica (CSS) particles of the invention were testing for anti-bacterial activity using the resazurin anti-bacterial test assay wherein the reduction of resazurin is a measure of reduction of bacterial growth.

All solutions are measured for the bacterial viability using resazurin microassay with Chemostat Inoculum (bacteria cocktail with *A. viscosus, S. oralis, V. parvula, L. casei*, and *F. nucleatum*) used in oral care product evaluation. Resazurin (7-Hydroxy-3H-phenoxazin-3-one 10-oxide) is a blue dye used as oxidation-reduction reaction, quantifies bacterial viability from color perception with respiring reaction effect.

Each experiment is conducted with live and dead bacterial cocktail with *A. viscosus, S. oralis, V. parvula, L. casei*, and *F. nucleatum* using TSB broth (trypticase soy broth) and ethanol respectively and they were added at proper ratio to generate standard curve from 100% live bacterial cocktail to 100% dead bacterial cocktail collecting at a total of 12 points.

The assay is performed using bacteria pellet from 1 ml Chemostat Inoculum and exposed with ¼ strength trypticase soy broth: test solution at 1:1 ratio in Eppendorf tube. After 1 hr incubation further bacteria growth was deactivated adding 1 ml D/E Broth with proper mixing and collected pellet was rinsed with 1 ml TSB broth to remove D/E broth completely (D/E=Dey-Engley). The last pellet was resuspended in 1.5 ml TSB broth & 100 µL amount was transfer in to 96 well plate with 100 µL of resazurin dye solution in 96 well plate. OD measurement was done with resazurin assay protocol after 3-5 min incubation at 37° C. to achieve perfect dye reaction.

The microassay is conducted once a day for 4-5 days considering the differences in bacteria from biology aspect from day to day. Final % bacterial viability represents average value. Present ingredients concentration is set to actual concentration in the Toothpaste formula.

TABLE 20

Resazurin anti-bacterial test (viability level)

| Test compositions | % of viable bacteria |
|---|---|
| Positive control (1% $ZnCl_2$ + water) | 4.88 |
| Na-CSS | 2.34 |

As can be seen from the data in Table 20, the core shell silica particles provide higher anti-bacterial activity than zinc chloride ($ZnCl_2$), a known anti-bacterial agent.

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising core shell silica particles and an orally acceptable carrier, wherein each core shell silica particle comprises a silica core, and a surface of the silica core etched with group I metal silicate; wherein the silica is selected from the group consisting of a precipitated silica, a fumed silica and a fused silica, wherein the core shell particles have a total cationic ion exchange capacity of from 0.5 to 5.0 meq/g, and wherein the composition comprises at least one of anti-caries agents, abrasives, sweetening agents, flavor agents, anti-calculus agents, at least one orally acceptable source of fluoride agents, or an active agent for treatment of a condition or disorder of hard or soft tissue of the oral cavity.

2. The oral care composition according to claim 1, wherein the Group I metal silicate comprises the formula $M_2SiO_3 \cdot xH_2O$, wherein M is a group I metal, and x is from 0 to 10.

3. The oral care composition according to claim 1, wherein the outer 10 nm depth of each particle has one of the following compositions:

$(SiO_2)_{30.30}Na_{0.41} \cdot 8.70H_2O$ $(SiO_2)_{30.67}Na_{0.36} \cdot 7.63H_2O$ $(SiO_2)_{23.25}[O^*_{11.73}H_{10.26}Na_{13.20}] \cdot 5.33H_2O$.

4. The oral care composition according to claim 1, wherein the d(0.5) value of the particles is from 5 nm to 50 µm, from 26 µm to 40 µm, 18 µm to 25 µm, from 10 µm to 15 µm or from 5 nm to 12 nm.

5. The oral care composition according to claim 2, wherein the $M_2SiO_3 \cdot xH_2O$ comprises a plurality of monolayers of $M_2SiO_3 \cdot xH_2O$, optionally wherein the number of monolayers is from 2 to 100, 2 to 40, 2 to 12 or 12 to 40 layers.

6. The oral care composition according to claim 1, wherein the oral care composition is in the form of a solid, paste, gel composition or liquid composition.

7. The oral care composition according to claim 1, wherein the orally acceptable carrier further comprises a humectant.

8. The oral care composition according to claim 1, wherein the composition further includes an ingredient selected from the group consisting of desensitizing agents, viscosity modifiers, diluents, surfactants, emulsifiers, foam modulators, pH modifying agents, mouth feel agents, colorants, preservatives, amino acids, anti-oxidants, thickeners, an adhesive agent, a whitening agent and combinations thereof.

9. A method comprising: administering an oral care composition according to claim 1 to an oral surface of a patient in need thereof.

10. The oral care composition according to claim 1, wherein the core shell silica particles have a d(0.5) value of 2.8 to 50 µm, where d(0.5) refers to the median particle size of a volume distribution that splits the distribution with half the population above and half below the diameter.

11. The oral care composition according to 10, wherein the d(0.5) value is 5 to 15 µm.

12. The oral care composition according to claim 2, wherein M is potassium.

13. The oral care composition according to claim 1, wherein the composition comprises at least one orally acceptable source of fluoride ions.

14. An oral care composition comprising core shell silica particles and an orally acceptable carrier, wherein each core shell silica particle comprises a silica core, and a surface of the silica core etched with group I metal silicate; wherein the silica is selected from the group consisting of a precipitated silica, a fumed silica and a fused silica, and wherein the core shell silica particles have a d(0.5) value of 2.8 to 50 µm, where d(0.5) refers to the median particle size of a volume distribution that splits the distribution with half the population above and half below the diameter, wherein the core shell particles have a total cationic ion exchange capacity of from 0.5 to 5.0 meq/g, and wherein the composition comprises at least one of anti-caries agents, abrasives, sweetening agents, flavor agents, anti-calculus agents, at least one orally acceptable source of fluoride agents, or an active agent for treatment of a condition or disorder of hard or soft tissue of the oral cavity.

15. The oral care composition according to claim 14, wherein the d(0.5) value is 5 to 15 µm.

16. The oral care composition according to claim 14, wherein the composition comprises at least one orally acceptable source of fluoride ions.

17. The oral care composition according to claim 14, wherein the metal silicate comprises the formula $M_2SiO_3 \cdot xH_2O$, wherein M is a group I metal, and x is from 0 to 10.

18. The oral care composition according to claim 17, wherein M is potassium.

* * * * *